United States Patent [19]
Dechene et al.

[11] Patent Number: 5,367,260
[45] Date of Patent: Nov. 22, 1994

[54] APPARATUS TO OBTAIN FLOW RATES (MELT INDEX) IN PLASTICS VIA FIXED FREQUENCY, PULSED NMR

[75] Inventors: Ronald L. Dechene, Boxford, Mass.; Thomas B. Smith, Atkinson, N.H.; Scott A. Marino, Haverhill, Mass.; Ronald J. Tache, Malden, Mass.; Ajoy K. Roy, Danvers, Mass.

[73] Assignee: Auburn International, Inc., Danvers, Mass.

[21] Appl. No.: 961,264

[22] Filed: Oct. 15, 1992

[51] Int. Cl.⁵ .................................................. G01R 33/20
[52] U.S. Cl. ........................................................ 324/307
[58] Field of Search ............... 324/300, 307, 309, 310, 324/311, 312, 313, 314, 316, 318, 322; 128/653.2, 653.5

[56] References Cited

U.S. PATENT DOCUMENTS

| | | | |
|---|---|---|---|
| 4,489,275 | 12/1984 | Sancier et al. | 324/315 |
| 5,015,954 | 5/1991 | Dechene et al. | 324/307 |
| 5,049,819 | 9/1991 | Dechene et al. | 324/307 |
| 5,111,145 | 5/1992 | Sepponen | 324/316 |

OTHER PUBLICATIONS

American Society for Testing and Materials document Designation: D 1238-90b, pp. 393-399, Table 5, p. 406, Table 2.

Primary Examiner—Michael J. Tokar
Attorney, Agent, or Firm—Edwin H. Paul; Jerry Cohen

[57] ABSTRACT

A pulsed NMR analysis system and process comprising an air curtain (137), sample throughput system (P, LI, V1, V2) and user system controls (104) to establish digitized free induction decay curves (C), from which components functions are determined using linear or nonlinear regression techniques to correlate the curve components to the target nuclei and to flow rates in plastic including MI and FRR for polyethylene and MF for polypropylene.

14 Claims, 5 Drawing Sheets

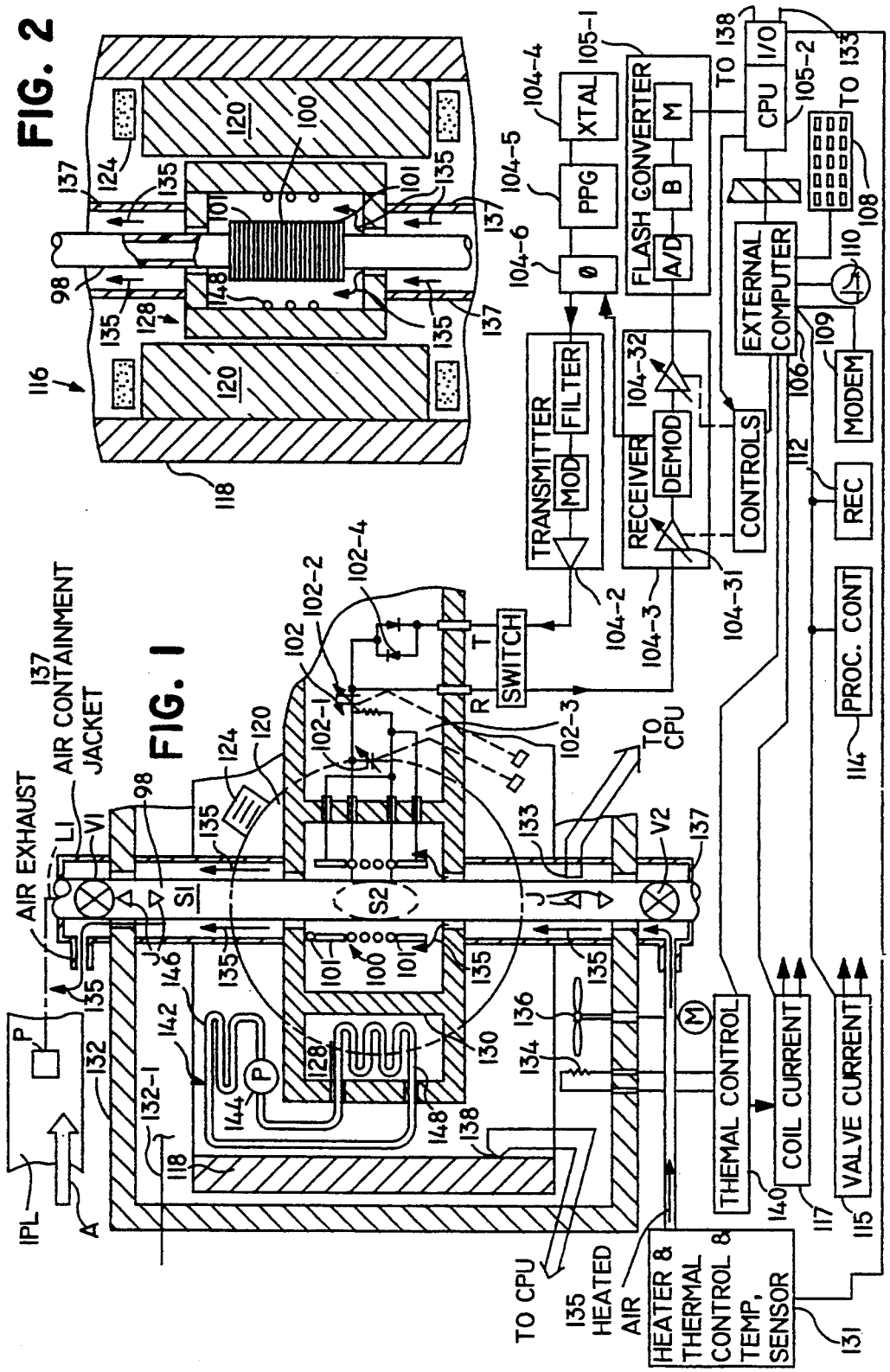

APPARATUS TO OBTAIN FLOW RATES (MELT INDEX) IN PLASTICS VIA FIXED FREQUENCY, PULSED NMR

CROSS REFERENCE TO RELATED APPLICATIONS

This application is closely related to the U.S. Pat. No. 5,015,954 issued on May 14, 1991 to Dechene et al., and to U.S. Pat. No. 5,049,819 issued Sep. 17, 1991 to Dechene et al., both entitled "Magnetic Resonance Analysis in Real Time, Industrial Usage Mode"; and to U.S. patent application Ser. No. 07/794,931 filed Nov. 20, 1991 entitled "Improved Magnetic Resonance Analysis in Real Time, Industrial Usage Mode"; to U.S. patent application Ser. No. 07/885,633 filed May 19, 1992, entitled "NMR Analysis of Polypropylene in Real Time", and to U.S. patent application filed Oct.13, 1992, entitled "Real time magnetic resonance analysis with non-linear regression means". All of these patents and patent applications are of common assignment with this application, and the disclosures of all are hereby incorporated herein by reference, as though set out at length herein.

FIELD OF THE INVENTION

The present invention relates to the analytic means relating a Nuclear Magnetic Resonance (NMR) free induction decay (FID) curve to the physical quantities of the target nuclei in the samples under test. More particularly, the present invention relates to regression means that provide correlation between the function equations derived from the FID and the types, properties and quantities of target nuclei in the sample under test.

BACKGROUND OF THE INVENTION

Pulsed NMR techniques are used in instruments for the measurement of the type, property and quantity of lattice bound and free, magnetically active nuclei within a sample. Some of the substances and properties that have been measured by NMR techniques are: moisture, polymers and copolymers, oils, fats and crystalline materials.

Pulsed NMR uses a burst or pulse of energy that is designed to excite the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. That is, the transverse magnetization associated with the excited nuclei relaxes back to its equilibrium value of zero. This relaxation produces a changing magnetic field which is measured in adjacent pickup coils. A representation of this relaxation is the FID curve.

The analysis method described herein and in the above related patents and applications is to decompose the FID waveform into a sum of separate time function equations. The coefficients of these equations are derived from the FID by use of a Marquardt-Levenberg (M-L) iterative approximation that minimizes the Chi-squared function—a technique well known in the art. Some of the time function equations found useful are: Gaussians, exponentials, Abragams (Gaussian) * (sin(t)) * (1/t), modified Gaussian ((Gaussian) * (cos (sqrt (t))) *1/sqrt (t))) and trigonometric. From these time functions a set of parameters is calculated. Some of these parameters are ratios of the y-axis intercepts, squares and cross products of these ratios, and decay times for each of the time curves.

In addition the sample temperature may form the basis for another parameter. A limitation exists since any temperature difference between the sample and the sample chamber and the local environment will cause the sample temperature to change during the measurement. This changing temperature creates errors which may become significant. Such errors have been observed when measuring and then predicting the solids content in processed cheese, and, similarly, various flow rate measurements in polyolefins.

The first temperature measuring problem is the measuring probe which is inserted into the sample. But placing the probe disturbs the sample flow, possibly blocking or bridging the flow during filling and emptying, and the probe itself may cause the sample temperature to change. In short, errors will occur. Infrared temperature sensing techniques suffer from the need to place a window viewing the sample, allowing energy to escape through the window (in order to sense the temperature) and so causing errors.

Melt Index (MI) is an industry term for polyethylene defined as the flow rate obtained under Condition 190/2.16, as found in Note 19 of ASTM (American Society for testing and Materials) No. D1238-90b, and Flow Rate Ratio (FRR) is similarly defined for polyethylene as the dimensionless number derived by dividing the flow rate at condition 190/10 by the flow rate at condition 190/2.16, as found in Paragraph 8.3, page 396 of ASTM No. D1238-90b. In some instances, the logarithm of FRR is used in lieu of FRR. Melt Flow (MF) is an industry term for polypropylene defined as the flow rate at condition 230/2.16 of the ASTM No. D1238-90b. It should be noted that the above are not all universally accepted as indicated in above referenced Note 19. This note suggests, other than MI for polyethylene, only the use of flow rates for all materials regardless of the condition used.

Melt index (MI), flow rate ratio (FRR) and melt flow (MF) measurements are routinely done by technicians using manual or automated plastometers that are slow and tedious to use. There is a need to automate and develop on-line techniques fort the rapid and accurate measurements of MI, FRR and MF, as these are important parameters that are widely used for quality control purposes.

Section 4.3 of the above referenced ASTM D1238-90b specification publication states, "The flow rate obtained with the extrusion plastometer is not a fundamental polymer property. It is an empirically defined parameter critically influenced by the physical properties and molecular structure of the polymer and the conditions of measurement. The rheological characteristics of polymer melts depend on a number of variables. Since the values of these variables occurring in this test may differ substantially from those in large-scale processes, test results may not correlate directly with processing behavior." The plastics industry measures flow rates as described in the ASTM specification and infers the physical and chemical properties such as crystallinity, average molecular weight and the molecular weight distribution. Since the flow rates are not fundamental properties of plastics—the physical properties can only be inferred.

It is a principal object of this invention to measure physical properties of plastics and relate those properties back to flow rates by calibration with known samples.

Polyethylene, including linear polyethylene may be considered as having three major components, namely, a crystalline, an interfacial and an amorphous. For material with higher MIs, the crystalline region is efficiently packed providing less interfacial content (a parameter). In amorphous regions in higher MI samples, an extra degree of randomness results in greater free volumes. This means that methyl groups at the ends of the polymer chains or localized chain units involving 10–15 bonds undergo less restricted motion in material with higher MIs. Better averaging of dipole-dipole interaction (due to enhanced motion) therefore results in a longer time constant (a parameter) for decay of NMR signals originating from amorphous regions. Conversely, shorter time constants result in materials with lower MIs. Similar observations have been made for polypropylene and other plastics.

But, relating these previously mentioned parameters, quantitatively and qualitatively, back to the species of target nuclei is required. In the above referenced patent applications, the system is calibrated with known samples, and a regression equation is generated which relates the parameters to the types, properties and quantities of the target nuclei. An unknown sample is introduced and the time functions are derived via the M-L iteration, and the parameters are calculated. The parameters are "regressed" via the regression equation to yield the types, properties and quantities of target nuclei in the unknown sample. That is, the measured parameters from the unknown FID are used with the regression equation, and the types, properties and quantities in the unknown sample are determined. It is to be understood that the multidimensional regression equation may not be graphically represented, and that the regression equation may be non-linear. As a simple regression technique example, consider that the grade point average of each of the students at a college were related to that student's SAT score and high school standing (forming a three dimensional space). The line formed is a "regression line" (which may be graphed). A new student's grade point average may be predicted by placing the student's SAT and high school standing on the "regression line" and "reading" the grade point average.

It is a principal object of the present invention to obtain flow rates for plastics, (melt index and flow rate ratio for polyethylene, and melt flow for polypropylene) via NMR techniques.

It is another object of this invention to compensate for temperature changes in the sample under test.

It is yet another object of this invention to relate the type, property and quantity of target nuclei of interest accurately and precisely.

SUMMARY OF THE INVENTION

The above objects are met in an NMR system that effects a reliable extraction of free induction decay data in a way that is practical in a wide variety of applications, including industrial and medical. The NMR system is calibrated by measuring known samples of target nuclei and, from the FIDs generated, forming a multi-dimensional, linear or non-linear regression relationship to the types, properties and quantities of target nuclei and then to flow rates in plastics (melt index and flow rate ratio for polyethylene, and melt flow for polypropylene). The FIDs are decomposed or transformed into a set of equations for the calibration samples from which a set of parameters is generated. From these parameters a regression function is calculated relating the type, property and quantity of target nuclei to the parameters. The FID of an unknown sample is decomposed or transformed as were the known samples, the parameters are calculated and these parameters are used with the linear or non-linear regression function to determine the type, property and quantity of target nuclei in the unknown sample. In a preferred embodiment, the FID is decomposed into multiple time equations via M-L processes and parameters are calculated for each of these time equations. In another preferred embodiment the parameters are non-dimensional in order to eliminate concentrations and the like from the measurements.

The present invention may be used to advantage with any number or type of time or frequency functions derived from an FID waveform, including Fourier transform functions.

The above object of providing better temperature stabilization is met by immersing the sample in a thermal environment that matches the sample temperature, thereby eliminating thermal gradients. In a preferred embodiment the sample tube is surrounded with temperature controlled air (an air curtain)- In a preferred embodiment the sample temperature is measured by any of a variety of means, including but not limited to: semiconductor junctions, thermocouples, thermistors, or infra red sensors. The temperature is measured at two different times during the sample resident time in the sample chamber. The air curtain temperature is incrementally adjusted at the end of each NMR measuring cycle so as to force the change in sample temperature to approach zero during the next NMR measuring cycle. If the air curtain temperature is maintained equal to the sample temperature, no heat energy will flow between the sample and the air curtain and the sample temperature during measuring will remain constant. The assumption that the next sample will be at essentially the same temperature as the preceding sample is valid for virtually all on-line operations wherein this invention maybe used. Other objects, features, and advantages will be apparent from the following detailed description of preferred embodiments taken in conjunction with the accompanying drawing(s) in which:

BRIEF DESCRIPTION OF THE DRAWING(S)

FIGS. 1–2 is a block/schematic drawing of a pulsed NMR system suitable for measuring a range of industrial materials, with an air curtain implementation, FIG. 3 is a graphical representation of an FID and its component curves measured for polyethylene, FIG. 4 is a graph of NMR (IMR) measurements of MI compared to ASTM laboratory measurements of MI, FIG. 5 is a flow chart of a preferred embodiment of the present invention, and FIG. 6 is a flow chart of the steps to establish an effective industrial measurement.

DETAILED DESCRIPTION OF PREFERRED EMBODIMENTS

Figure 3:
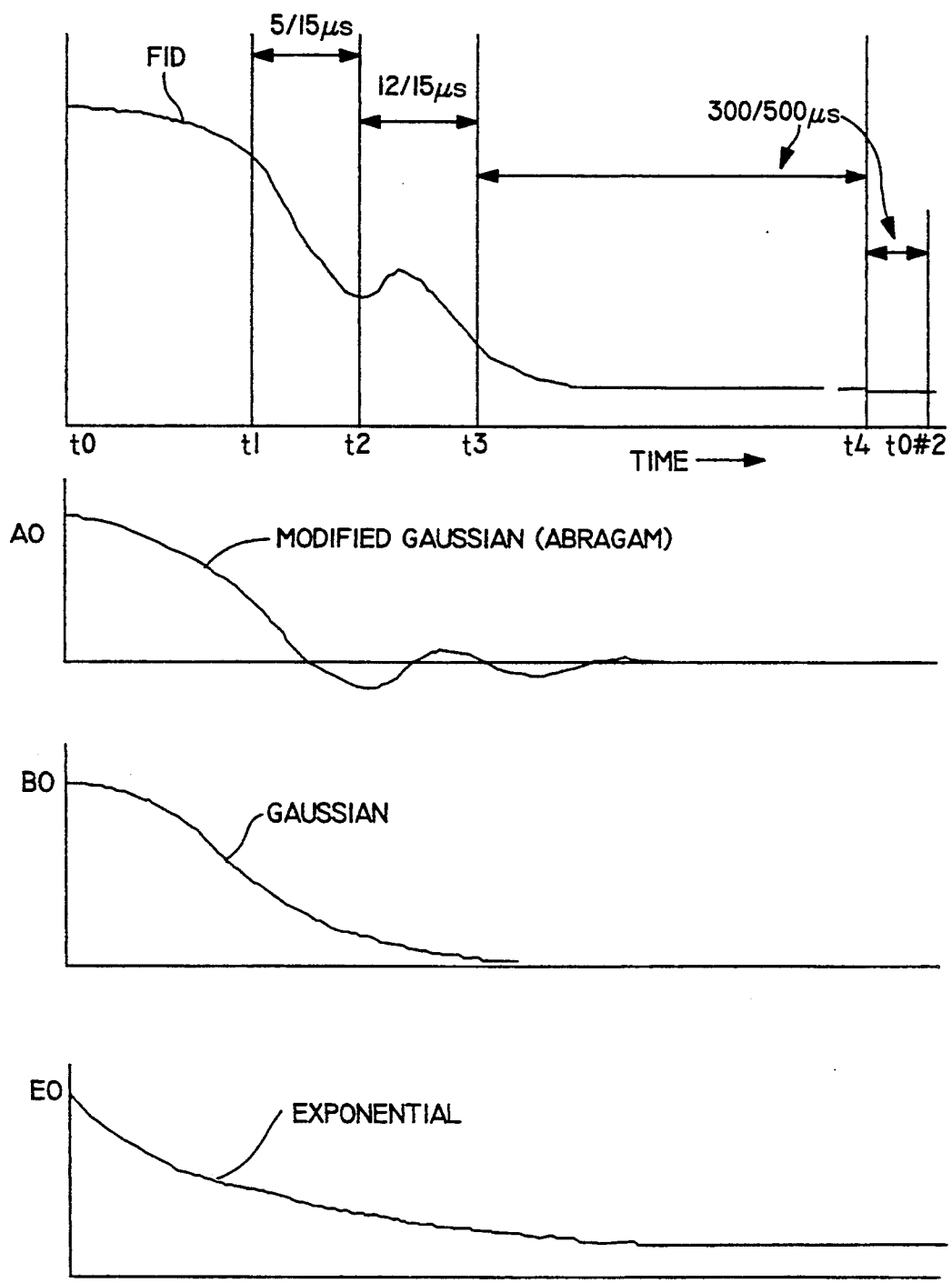

FIG. 1 shows transverse and cross sections with block diagram inserts of an NMR apparatus and method where the present invention may be used to advantage.

An industrial process line IPL has material flowing as indicated by arrow A. Some of the material is captured by a probe P and fed through an inlet line LI to a sample region S1. The region is defined by a tube 98 typically about 30 cm long made of an essentially non-magnetic, nonconducting material which does not itself generate substantially interfering FID signals (glass, certain ceramics, certain plastics or hybrids may be used). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 110 and utilized in 112 and/or 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and over-all mass related to each other to minimize harmonics and other interferences with a signal emitted from coil 100 to a sample and/or returned from the sample for pick-up by coil 100 and its tuned circuit 102 and transmit/receive controller 104.

The magnetic assembly 116 including yoke 118, and other parts therein as shown on FIGS. 1-2, is in turn contained in an environmental control chamber 132 with optional inert gas fill and purge controls (not shown), an internal gas heater 134, a motor M driving fan 136, and a temperature sensor 138 which can be applied to the yoke or other detection region whose temperature is reflective of the temperature at pole pieces 120 and in the sample region therebetween. A thermal controller 140 processes temperature signals from 138 to adjust heating/circulation at 134/136 as a coarse control and to adjust current through the Helmholtz coils 124 at magnet pole pieces 120 as a sensitive and fast fine control, as well as implementing general control instructions of computer 106. Further thermal stabilization may be provided by a temperature controlled air curtain consisting of temperature controlled air 135 circulating inside an air containment jacket 137, completely surrounding the sample being measured. The temperature of the air curtain is controlled by the heater thermal control and temperature sensor 131 according to control parameters received from CPU 105-2(I/O). Sample temperature is measured by temperature sensor 133 from which external computer 106 determines the desired air curtain temperature set point to be conveyed to heater thermal control 131.

The strength, consistency and constancy of the magnetic field between poles 120 in the region S2 of the sample is thus controlled by a uniform base magnetic field in the entire region S2. The Heimholtz coils 124 are energized by the coil current controller 117 to accurately trim the final magnitude of the field in which the sample is placed. This field is the vector addition of the fields due to the magnet poles 120 and the Helmholtz coils 124. The controller 117 sets the current through the Helmholtz coils 124 using current generators. The coils 124 are wound around the magnet pole pieces such that the magnetic field created by the current in the coils 124 can add to or subtract from the field created by the magnet pole pieces. The magnitude of the current through the coils 124 determines the strength the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved, and then setting the Helmholtz current off resonance by a given offset, of about 0.1-3 KHz.

The major elements of electrical controls are tuner 102, including coils 100 and 101 and variable capacitors 102-1 and 102-2, resistor 102-3 and diodes 102-4 and constructed for tuning to Q of twenty to sixty to achieve coil 100 resonance, and control 104 including a transmit/receive switch 104-1, a transmitter 104-2 and receiver 104-3, a crystal oscillator 104-4, gated pulse generator (PPG) 104-5, and phase shifter 104-6. The crystal provides a nominal twenty Megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed at least 12 bit flash A/D converter 105-1 and internal (to the instrument) CPU element 105-2, which provides data to an external computer 106 which has a keyboard 108, monitor 110, modem 109, recording elements 112 and process controller elements 114, e.g., for control of valves V1, V2 via valve controls 115 and/or to coil current controls 117, all via digital-analog converters (not shown).

The analog signal FID curve is conditioned by a Bessel filter which acts as a pre-filter and an anti-aliasing filter as the subsequent sampling is done at 10 MHz. After digitization the signal may be time smoothed by a Fast Fourier transform, Savitsky-Golay or other filter program. The combination of these filters produces a relative improvement in signal to noise ratios which enhances the accuracy of the system.

The excitation of coil 100 and excitation-precession of the sample's proton content and subsequent relaxation/decay produces a received FM signal that, after demodulation, controlled gain amplification, and A/D conversion produces the free induction decay (FID) curve.

Referring to FIG. 3, the digitized FID curve data for polyethylene or polypropylene, respectively, are transmitted to the external computer 106 where a program finds the best coefficients of the component curves to fit each digitized FID curve. In this preferred embodiment there are three component curves, a Gaussian, a modified Gaussian and an exponential. Other preferred embodiments have more or less than three component curves and other curve types. The determination of the types of curves which make up the FID curve is important because, once the curves are known, they can be extended back to a time origin (shown as $A_0$, $B_0$ and $E_0$ at t0, i.e., excitation of a Cycle 1), which is close to the center of the transmitted burst signal. This is important since there are saturation effects of the instrument's electronic gear which occur during and immediately after the excitation burst signal. During this time, measurements cannot be accurately taken, yet the area of interest under the curve, which is a measure of the number of nuclei in the sample, extends from the immediate end of the excitation burst to where the curve is toe small to be digitized or it is in the noise.

The entire curve is decomposed into component curves and these curves are fitted to the data by an iterative process based upon the Marquardt-Levenberg (M-L) approximation technique applied automatically through a structured realization in software. This technique is used to determine the magnitude of all the parameters, constants, frequencies, etc. which best fit the FID curve. This is an iterative technique where the entire curve is determined at once. The M-L iteration process performs the curve fitting by attempting to minimize the Chi-Squared error function (the sum of the squared differences between the measured data points and the data points from the derived equation). The results of the M-L approximation are accepted if the Chi-Squared error is small enough, if not, the M-L fitting procedure may be reapplied with a different set of starting assumptions. If this process also fails, the sample is discarded and a new sample obtained. The M-L technique is documented in the following references: *Ind. Appl. Math.*, vol. 11, pp. 431–441 by D. W. Marquardt, 1963; *Data Reduction and Error Analysis for the Physical Sciences* (New York, McGraw Hill), Chapter 11 by Philip R. Bevington, 1969; and *The State of the Art in Numerical Analysis* (London: Academic Press, David A. H. Jacobs, ed 1977), chapter III.2 by J. E. Dennis. As applied to the measurement regime of interest herein, in a preferred embodiment of the present invention, the selected parameters taken from the derived curves are the y-axis intercept ratios, time constants, frequency terms and other parameters described below.

Other known-in-the-art iterative techniques which may be applied instead of or with the Marquardt-Levenberg, include: Gauss-Newton and "steepest descent" ( found in the above J. E. Dennis reference), Newton-Raphson (known in the art), or like techniques, including combinations of these techniques.

One of the major difficulties in making use of iterative curve fitting techniques (such as Marquardt-Levenberg) is their tendency to reach incorrect solutions. Such solutions frequently (but not always) contain parameters which would imply a negative quantity of protons or an exponential "decay" which grows with time. These incorrect solutions lead to serious errors in the result found for a physical sample, for example, the density or flow rates in polyethylene or the quantity of xylene solubles or melt flow in polypropylene.

The usual methods of handling these difficulties have been:

(1) have a human evaluate the result and eliminate those solutions that are theoretically impossible, and/or (2) put a series of upper and lower bounds on each parameter beyond which the fitting procedure is forbidden to go.

In an on-line situation where readings are generated every few minutes, the first approach obviously cannot be used, and in the case of polyethylene and polypropylene the second approach fails because the bounds for each parameter depend on the actual values of the other parameters (note that for polypropylene and polyethylene the model equations involve ten or more parameters).

We have evolved a technique referred to as Marquardt Reference Ratio (MRR) to handle this difficulty. MRR is a ratio although other techniques (differences, for example) could be used/(see MRD below).

As discussed herein, the techniques to find a property of an unknown sample include calibration by applying the M-L technique to reach solutions for a group of FIDs from samples with known properties. The various amplitudes and time constants in the solutions are combined to produce a number of ratios, cross products and higher order parameters. These parameters may undergo various non-linear transformations and are finally regressed multi-dimensionally to obtain the coefficients of the regression equation to use in predicting a property of an unknown sample, say, for example, density. Each of the parameters contributes to the overall prediction of density. However, in the nature of things, these parameters tend to be correlated among themselves; e.g., a large crystalline content must necessarily correspond to a small amorphous content (comparing the modified Gaussian to the exponential in the polyethylene FID solution). This means that overlapping density information is contained in many of the parameters used in the regression equation. Similar arguments apply to other properties, such as xylene solubles in polypropylene.

To make use of this correlation (continuing the density example), the parameters are divided into subgroups (two roughly equal groups in a preferred embodiment) and each of these groups is regressed on density to obtain two further predictions of density based on each subgroup, as follows:

D1 (density)=F(subgroup 1)
D2 (density)=G(subgroup 2)

Because of the correlation, discussed above, among the parameters, the functions F and G (above) result in predictions D1 and D2 which are only slightly less accurate than the density prediction based on the entire set of variables. The ratio (MRR) or the difference (MRD) are formed as follows:

MRR=D1/D2=F/G
MRD=D1-D2=F-G

MRR has a nominal value of one and MRD zero. MRR and MRD are sensitive measures of whether or not a particular proposed M-L solution for an unknown sample belongs to the set of (calibrated) data from which the functions F and G were derived. If the calculated ratio or difference of D1 and D2 for a proposed M-L solution for fitting the FID of an unknown sample lies outside reasonably well-defined limits (usually ±3 sigma), the proposed M-L solution may be assumed to be bad and is discarded.

Once the equation of the FID curve is known, each component curve can be extrapolated back to the midpoint of the excitation signal to establish the intercept of each said component curve.

The resulting data utilized in the computer 106 (FIGS. 1-2) is the equation for the FID curve as composed of a number of component curves. Each of these curves (and their intercepts) has been experimentally and theoretically related to particular nuclei of interest. In particular, when the FID curve equation is determined, the ratios of the y-axis intercepts, the cross product and squares of these ratios and the decay times for each of the curve components, the product temperature and a cosine term form a multidimensional model.

Calibration of the system is accomplished by measuring a number of known samples and using the M-L technique to derive the model equation constants associated with each known sample. Various non-linear transforms may then be applied to these constants, usually with the goal of linearizing their relationship to the dependent (i.e., predicted) parameter. Useful non-linear functions include exponential, logarithmic, powers and cross products of the independent (i.e., measured) parameters.

Figure 4:
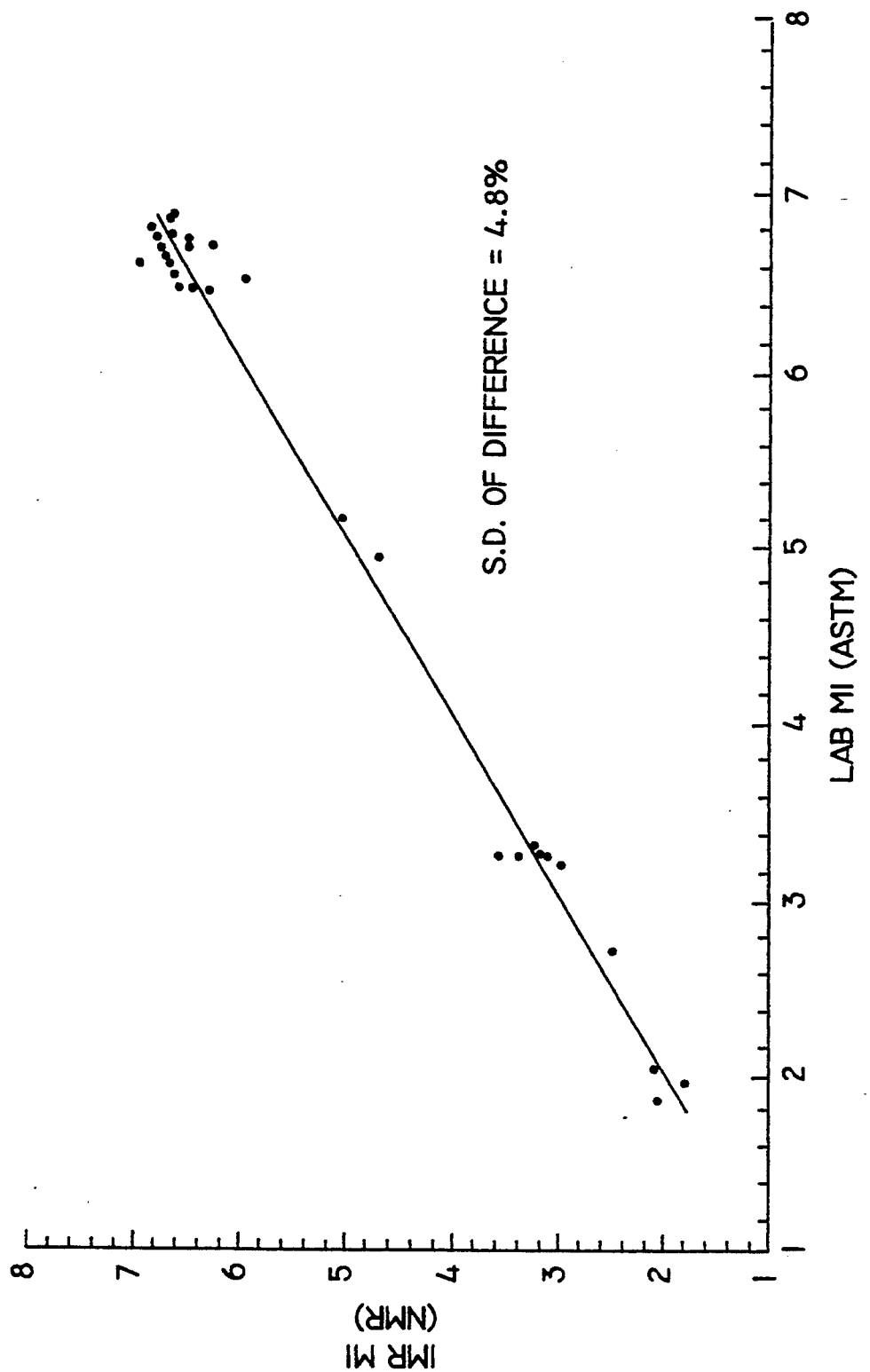

FIG. 4 is a graph showing on-line MI results of the IMR (same as NMR) method compared with the laboratory ASTM MI method. The IMR MI results were determined from the FID analysis and model equations as noted previously. The standard deviation between the IMR MI and the ASTM MI is 4.8%. This standard deviation includes errors due to both the IMR and ASTM measurement methods.

Figure 5:
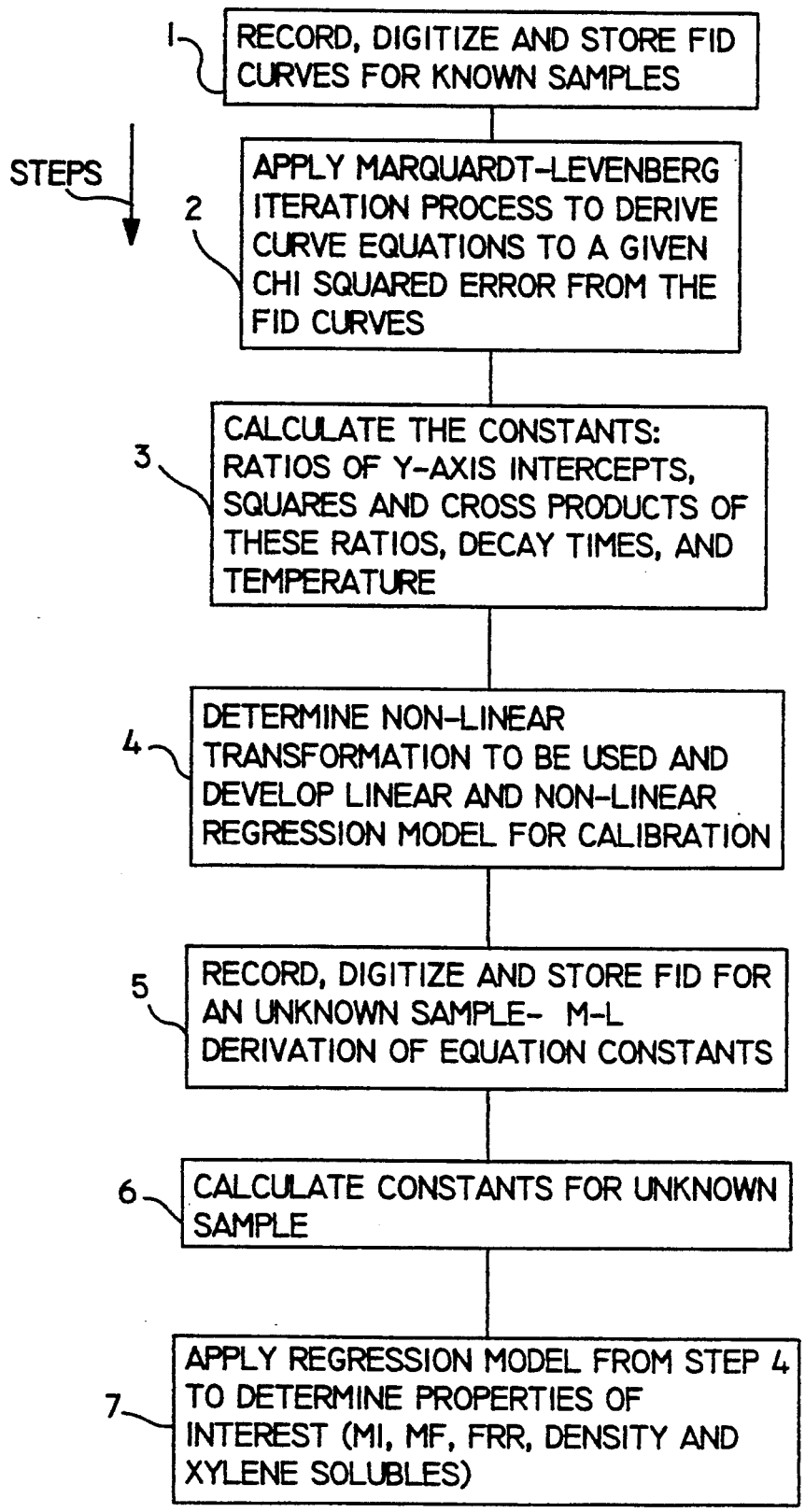

FIG. 5 is a flow chart of the steps used in a preferred embodiment of the present invention. The first step is to measure samples with known types, properties and quantities of target nuclei, including flow rates in plastics (MI and FRR in polyethylene and MF in polypropylene). The FID curve is digitized via a flash converter of at least 12 bits and preferably 14 bits accuracy and stored in computer memory. The next step is to apply the M-L iterative process to derive curve coefficients from the stored FIDs to a given Chi-Squared error. In step three the ratios of Y-axis intercepts, squares and cross products of these ratios, decay times and temperatures are calculated. In the next step, the various non-linear transformations to be used are determined, and the types, properties and quantities of target nuclei in the known samples are related to the constants by a regression against these transformed parameters—the regression equation. Step five is to record and digitize the FID for an unknown sample and derive the curve coefficients. The parameters are calculated for the unknown, and these parameters with desired non-linear transforms are used in the regression equation to determine the actual type, property and quantity of target nuclei (and flow rates) in the unknown sample. Ratios are used since constants with dimensions of weight would require the samples to be carefully weighed before measuring.

Figure 6:
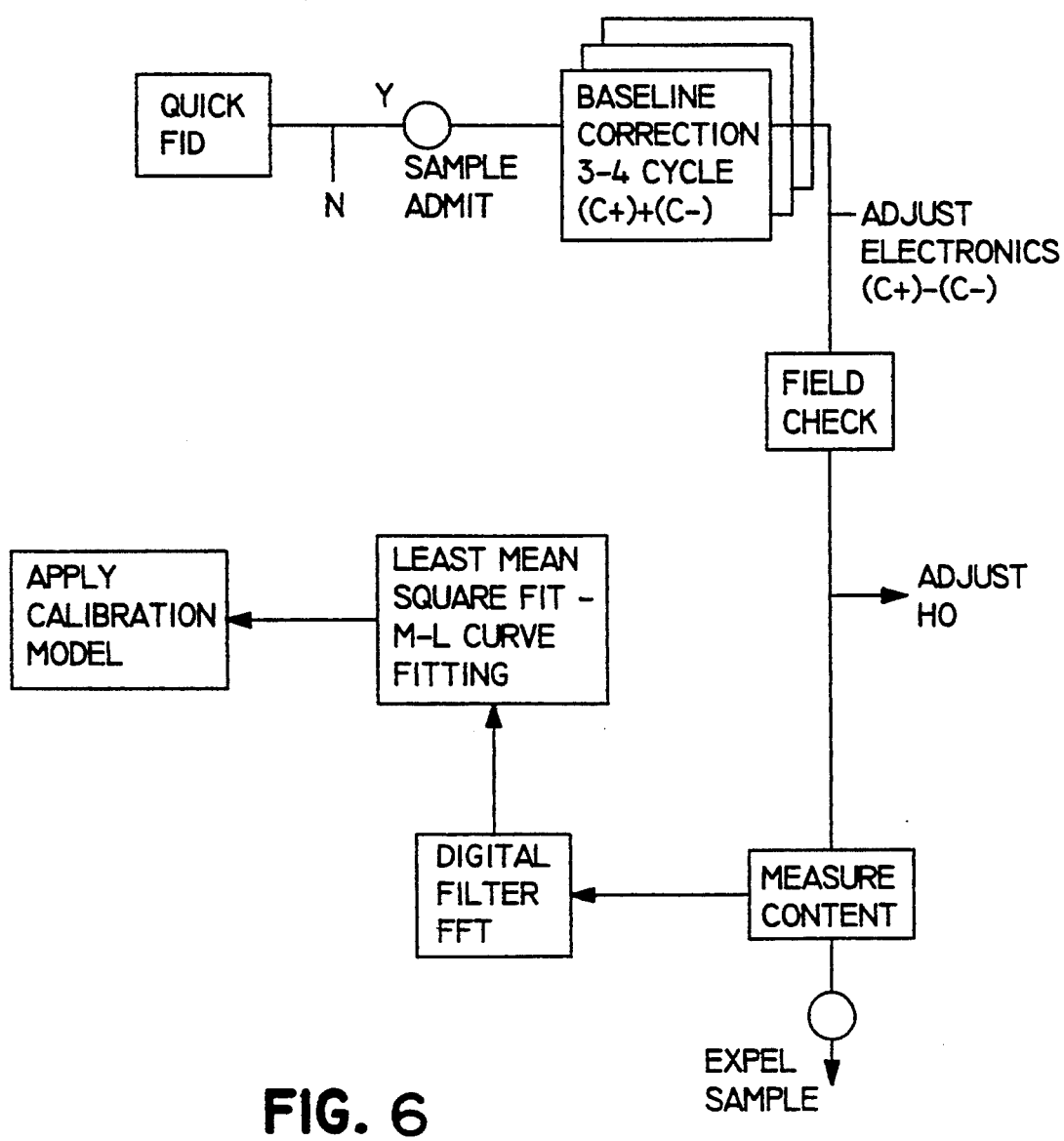

FIG. 6 is a flow chart showing the steps of measurement to establish effective industrial measurement. A single FID curve is established to see if the sample area is clear (Quick FID) in an abbreviated cycle of attempting to establish an FID curve. If the sample region is not clear (N), measurement is interrupted to allow valve V2 to open and jets J and gravity to clear the region. A new Quick FID step establishes clearance. Then another sample is admitted by closing valve V2, opening valve V1 and making such adjustments of probe P and line L1 as may be necessary to assure sample acquisition. Jets J adjust and stabilize the new sample.

The air curtain described above may be used to establish very coarse and less coarse thermal controls countering sample and ambient temperature variations.

An electronic signal processing apparatus baseline is established in 3-4 cycles (each having (+) and (−) sub-cycles with addition of (C+) and (C−) to detect a baseline offset and compensate for it). It would be feasible to avoid this baseline step determination and simple deal with it as an additional parameter (i.e. eleventh dimension in the M-L analysis, but this would increase iteration time). Further adjustment is established by coils 124 to adjust H0 (i.e., resonance) and this is enabled by ten to twenty field check cycles of FID curve generation. The (C−) FID is subtracted from the (C+) FID, (this process eliminates small baseline offsets) to obtain a workable digitized FID signal—which has a maximum value at resonance. H0 is adjusted via coil current generator 117 and coils 124 until such maximum is achieved, and then H0 is changed to offset the system by a given amount of about 0.1 to 3 KHz.

Then five to one hundred measurement cycles are conducted to obtain a useable measurement. Each of these five to one hundred cycles involves a modulated transmission/reception/flash A-D conversion, and storage of data. The curves are then averaged for M-L curve fitting, and the above listed intercepts and ratios are established. Similar cycles, but somewhat abbreviated can be applied for Quick FID, field check and baseline correction purposes. Each of the sub-cycles [(+) and (−)] of each such cycle involves a capture and utilization of thousands of FID points in data reduction. Each sub-cycle occurs on the order of a second and the number of such sub-cycles employed depends on the desired smoothing and signal to noise ratio (S/N); generally S/N improves in a square root relationship to the number of cycles.

As noted in above cited Dechene et al. references, in requiring greater accuracy and reliability, sample tube composition can distort readings. If glass is not used (and it is preferred to avoid glass in industrial usage), then the replacement should not be a hydrocarbon plastic. But fluorocarbons can be effective in several applications since signals from fluorine appear far from resonance. These signals can be distinguished from hydrogen at the levels of sensitivity required and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptably for polymer measurements. In all such cases the point is to avoid sample containers with species that can couple with transmitted energy and generate a FID decay curve mimicking the samples.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. In a nuclear magnetic resonance system for measuring flow rates in plastics comprising:
   (a1) means for accessing and then (a2) removing successive samples of plastic material from an industrial process and then (a3) placing them in a sample measuring region, (b) means for applying a base magnetic field to said region to effect precession of nuclei of the samples of material therein, (c) means for applying a local excitation pulse of energy to said region to modify the precession, (d) said means (c) including transmit-receive antenna coil means and means for translating a received relaxation signal detected at the coil means in the form of a free induction decay, said relaxation signal being based on free induction decay of the sample material nuclei, (e) means for digitizing the free induction decay and analyzing the free induction decay into component equations, (f) means for further analyzing the component equations comprising means utilizing an iteration technique for converting said digitized version of said free induction decay into the component equations of said decay and establishing said zero intercepts and time parameters of said equations corresponding to flow rates in plastics, by forming a calibration relationship between the component equation parameters and known flow rates of known plastics, including MI and FRR for polyethylene and MF for polypropylene, means to input a sample temperature set point, means, responsive to said set point, to maintain said sample temperature at about said set point throughout said sampling and nuclear magnetic resonance measuring, and then discarding the samples from said region.

2. A system as defined in claim 1 wherein said iteration technique comprises a Marquardt-Levenberg technique for converting said digitized version of said free induction decay into the time equation of said decay curve and establishing said zero intercepts and time characteristics of said curve.

3. A system as defined in claim 1 wherein said iteration technique comprises a Gauss-Newton technique for converting said digitized version of said free induction decay into the time equation of said decay curve and establishing said zero intercepts and time characteristics of said curve.

4. A system as defined in claim 1 wherein said iteration technique comprises a Newton-Raphson technique for converting said digitized version of said free induction decay into the time equation of said decay curve and establishing said zero intercepts and time characteristics of said curve.

5. A system as defined in claim 1 wherein said iteration technique comprises a "steepest descent" technique for converting said digitized version of said free induction decay into the time equation of said decay curve and establishing said zero intercepts and time characteristics of said curve.

6. A system as defined in claim 1 wherein means for analyzing the free induction decay components corresponding to types, properties and quantities of target nuclei of the sample materials and flow rates in plastics (MI and FRR for polyethylene and MF for polypropylene) comprises: means for establishing calibration curves wherein the zero intercepts and time constant characteristics of said decay curve components of standard samples are related in a non-linear function to the known physical types, properties and quantities of target nuclei in said standard samples and flow rates in plastics (MI and FRR for polyethylene and MF for polypropylene), and means for comparing via said non-linear regression function said known sample zero intercepts and time characteristics to the zero intercepts and time characteristics of an unknown sample wherein said physical types, properties and quantities of nuclei of interest and flow rates in plastics (MI and FRR for polyethylene and MF for polypropylene) are read from the non-linear regression equation.

7. A system as defined in claim 6 wherein said means for comparing said calibration curves to the decay curve of an unknown sample comprises a non-linear regression analysis.

8. A method for measuring flow rates in plastics in industrial processes utilizing magnetic resonance comprising the steps of:

accessing and removing successive samples of plastic material from an industrial process placing said samples in a sample measuring region, applying a base magnetic field to said region to effect precession of nuclei of the samples of material therein, applying a local excitation pulse of energy to said region to modify the precession, receiving and translating a free induction decay signal, said free induction decay signal generated by the relaxation of the sample material nuclei after the end of said local excitation pulse, digitizing and analyzinq the free induction decay signal into component equations of the free induction decay signal, said analyzing comprising:

applying an iteration technique to the digitized free induction decay signal wherein said digitized signal is separated into a plurality of component curves.

determining the equations of the decay curve components in digital form and parameters defining the component equations, including zero intercepts and time Parameters of said equations forming calibration relationships between zero intercepts and time parameters of component equations to known flow rates in known plastics, and relating the zero intercepts and time parameters of the sample, to flow rates in plastics, including MI and FRR for polyethylene and MF for polypropylene, and measuring the temperature of said industrial process material heating a volume of air, responsive to said measured temperature, circulating said heated air around said .sample measuring region, wherein said sample maintains about constant temperature throughout said sampling and nuclear magnetic resonance measuring, and discarding said sample from said region.

9. A process as defined in claim 8 wherein the iteration technique comprises a Marquardt-Levenberg technique applied to the digitized decay curve wherein said digitized curve is separated into a plurality of component curves.

10. A process as defined in claim 8 wherein the iteration technique comprises a Gauss-Newton technique applied to the digitized decay curve wherein said digitized curve is separated into a plurality of component curves.

11. A process as defined in claim 8 wherein the iteration technique comprises a Newton-Raphson technique applied to the digitized decay curve wherein said digitized curve is separated into a plurality of component curves.

12. A process as defined in claim 8 wherein the iteration technique comprises a steepest descent technique applied to the digitized decay curve wherein said digitized curve is separated into a plurality of component curves.

13. A process as defined in claim 8 wherein the component equations are time equations and relating the zero intercepts and the time characteristics to the type, property and quantity of target nuclei of the sample materials and flow rates in plastics, including MI and FRR for polyethylene and MF for polypropylene comprises:

generating non-linear regression curves relating the zero intercepts and time characteristics of the decay curve components of standard samples to known type, property and quantities of target nuclei in said standard samples and flow rates in plastics (MI and FRR for polyethylene and MF for polypropylene), and comparing said zero intercepts and time characteristics measured from an unknown sample to said non-linear regression curve wherein said types, properties and quantities of nuclei of interest contained in said unknown sample and flow rates in plastics (MI and FRR for polyethylene and MF for polypropylene) are calculated from the non-linear regression equation.

14. A process as defined in claim 13 wherein said means for comparing said calibration curves to the decay curve of an unknown sample comprises a regression analysis.

* * * * *